(12) United States Patent
Kanios et al.

(10) Patent No.: US 7,063,859 B1
(45) Date of Patent: Jun. 20, 2006

(54) BARRIER FILM LINED BACKING LAYER COMPOSITION AND METHOD FOR TOPICAL ADMINISTRATION OF ACTIVE AGENTS

(75) Inventors: David Kanios, Miami, FL (US); Juan A. Mantelle, Miami, FL (US); David Houze, Coconut Grove, FL (US)

(73) Assignee: Noven Pharmaceuticals, Inc., Miami, FL (US)

( * ) Notice: Subject to any disclaimer, the term of this patent is extended or adjusted under 35 U.S.C. 154(b) by 0 days.

(21) Appl. No.: 10/245,943

(22) Filed: Sep. 18, 2002

Related U.S. Application Data

(63) Continuation-in-part of application No. 09/560,082, filed on Apr. 27, 2000, now abandoned.
(60) Provisional application No. 60/131,631, filed on Apr. 28, 1999.

(51) Int. Cl.
*A61L 15/16* (2006.01)
*A61K 9/70* (2006.01)

(52) U.S. Cl. ............... 424/448; 424/449
(58) Field of Classification Search .............. 424/449, 424/448
See application file for complete search history.

(56) References Cited

U.S. PATENT DOCUMENTS

| | | |
|---|---|---|
| 3,598,122 A | 8/1971 | Zaffroni |
| 3,598,123 A | 8/1971 | Zaffroni |
| 3,797,494 A | 3/1974 | Zaffroni |
| 3,814,095 A | 6/1974 | Lubens |
| 3,972,328 A | 8/1976 | Chen |
| 3,996,934 A | 12/1976 | Zaffaroni |
| 4,031,894 A | 6/1977 | Urquhart et al. |
| 4,307,717 A | 12/1981 | Hymes |
| 4,460,370 A | 7/1984 | Allison et al. |
| 4,538,603 A | 9/1985 | Pawelchak et al. |
| 4,588,400 A | 5/1986 | Ring et al. |
| 4,605,548 A | 8/1986 | Ushiyama et al. |
| 4,733,659 A | 3/1988 | Edenbaum et al. |
| 4,738,257 A | 4/1988 | Meyer et al. |
| 4,904,247 A | 2/1990 | Therriault et al. |
| 4,983,395 A | 1/1991 | Chang et al. |
| 4,994,049 A | 2/1991 | Latzke et al. |
| 4,994,267 A * | 2/1991 | Sablotsky ............... 424/449 |
| 5,006,342 A | 4/1991 | Cleary et al. |
| 5,008,110 A | 4/1991 | Benecke et al. |
| 5,032,207 A | 7/1991 | Sablotsky et al. |
| 5,176,916 A | 1/1993 | Yamanaka et al. |

(Continued)

FOREIGN PATENT DOCUMENTS

| | | |
|---|---|---|
| WO | WO97//35564 A1 | 10/1997 |
| WO | WO98/34600 A1 | 8/1998 |
| WO | WO00/91718 A2 | 11/2000 |
| WO | WO 01/91718 A3 | 12/2001 |
| WO | WO01/91718 A2 | 12/2001 |

*Primary Examiner*—Thurman K. Page
*Assistant Examiner*—Blessing Fubara
(74) *Attorney, Agent, or Firm*—Jay G. Kolman, Esq.; Scott M. Oldham, Esq.

(57) ABSTRACT

A transdermal drug delivery device for topical application of active agents is disclosed. The invention comprises the use of a flexible and soft backing layer, in particular a cellular foam, having an inner surface and an outer surface, wherein an impermeable polymeric barrier film is affixed to its inner surface. The barrier film functions to anchor and support an active agent carrier composition disposed thereon, and to prevent passage of such composition into the backing layer. The system provides excellent flexibility and conformability for topical application to sites subject to frequent movement or which are greatly contoured. Methods of use are also disclosed.

16 Claims, 1 Drawing Sheet

U.S. PATENT DOCUMENTS

| | | |
|---|---|---|
| 5,186,939 A | 2/1993 | Cleary et al. |
| 5,234,957 A | 8/1993 | Mantelle |
| 5,332,576 A | 7/1994 | Mantelle |
| 5,356,372 A | 10/1994 | Donovan et al. |
| 5,405,486 A | 4/1995 | Sablotsky et al. |
| 5,446,070 A | 8/1995 | Mantelle |
| 5,474,783 A | 12/1995 | Miranda et al. |
| 5,503,844 A * | 4/1996 | Kwiatek et al. ............ 424/449 |
| 5,523,118 A | 6/1996 | Williams |
| 5,536,263 A | 7/1996 | Rolf et al. |
| 5,567,488 A | 10/1996 | Allen et al. |
| 5,629,014 A | 5/1997 | Kwiatek et al. |
| 5,634,201 A | 5/1997 | Mooring |
| 5,656,285 A | 8/1997 | Sablotsky et al. |
| 5,656,286 A | 8/1997 | Miranda et al. |
| 5,716,621 A | 2/1998 | Bello et al. |
| 5,741,510 A | 4/1998 | Rolf et al. |
| 5,782,787 A | 7/1998 | Webster |
| 5,827,213 A | 10/1998 | Jensen |
| 5,891,463 A * | 4/1999 | Bello et al. ................. 424/449 |
| 5,976,547 A | 11/1999 | Archer et al. |
| 6,165,499 A | 12/2000 | Kleinsorgen et al. |
| 6,277,400 B1 * | 8/2001 | Horstmann et al. ......... 424/448 |

\* cited by examiner

10

BARRIER FILM LINED BACKING LAYER COMPOSITION AND METHOD FOR TOPICAL ADMINISTRATION OF ACTIVE AGENTS

This application is and of application Ser. No. 09/560,082 filed Apr. 27, 2000 abandoned which claims benefit of provisional application No. 60/131,631 filed Apr. 28, 1999.

FIELD OF THE INVENTION

This invention relates to an improved drug delivery system for topical administration of active agents. More particularly, the invention relates to a flexible, soft backing layer lined with a barrier film, and methods of use thereof for transdermal delivery of active agents.

BACKGROUND OF THE INVENTION

The use of a device for providing continuous and controlled topical delivery of active agents through skin or mucosa is well known. These devices, often referred to as transdermal drug delivery systems, attempt to avoid and overcome many problems associated with other routes of drug administration—oral administration in which the drug may not be tolerated well by the digestive tract and is often required to be multiple daily dosed in order to achieve therapeutic levels (e.g., low bioavailability due to degradation or metabolism); administration by ointment, gel or cream in which the drug may be inadequately dosed or overdosed causing wide fluctuations in blood levels or therapeutic effect at the site of application, or may cause undesirable side effects of the absorbing tissues as well as interfering with the clothing and activities of the user; and administration by injection in which the delivery is typically unpleasant or painful and requiring assistance of a medical professional, leading to poor patient compliance especially in therapy for chronic diseases.

Generally speaking, transdermal drug delivery systems are commonly either reservoir-type or matrix-type devices. Both types of devices include a backing layer that forms the outer surface of the finished transdermal device and which is exposed to the environment during use, and a release liner or protective layer that forms the inner surface and which covers the adhesive means for affixing the devices to the skin or mucosa of a user. The release liner or protective layer is removed prior to application, exposing the adhesive means which is typically a pressure-sensitive adhesive. The active agent is located between the release liner and backing layer, usually solubilized or dispersed in a solvent or carrier composition.

In a reservoir-type device, the active agent is isolated from the adhesive means used to affix the device to the user. Traditionally, a reservoir system referred to a device having a pocket or "reservoir" serving to hold the active agent and was formed in or by the backing layer itself. Such a backing layer is impermeable, occlusive and typically rigid. A peripheral adhesive layer is then used to affix the device to the user. While such devices are still in use today, the term reservoir has become known as a device which employs one or more permeable layers, such as rate controlling membranes, and drug permeable adhesives layers, laminated over the reservoir (which is typically nothing more than another layer containing the drug in a carrier composition), in an effort to more effectively control the delivery rate of the active agent and attachment of the device to the user.

A matrix-type device generally comprises the active agent solubilized or dispersed in a carrier formulation which functions as both the drug carrier and the adhesive means of applying the system to the skin or mucosa. Such devices are described, for example, in U.S. Pat. Nos. 4,994,267; 5,474,783 and 5,656,286, assigned to Noven Pharmaceuticals, Inc., Miami, Fla.

Reservoir-type transdermal drug delivery systems tend to be bulkier and/or therefore less flexible and comfortable than matrix-type devices. The thicker and less flexible the device, the greater the tendency to wrinkle, fold and dislodge or loosen from the site of application. If a transdermal drug delivery system is to effectively deliver a therapeutic amount of active agent, it must remain in intimate contact with the skin or mucosa. Accordingly, reservoir-type devices work best on body areas that are flat or subject to the least amount of movement.

By reducing the overall thickness and bulk of reservoir-type systems, matrix-type devices offer improved flexibility and adherence with movement at the application site. The ability of the matrix-type device to conform to the application site and be comfortable to the user is essentially determined by the material selected as the backing layer.

The backing layer serves to retain and maintain the active agent carrier composition disposed on it in a defined size and shape, imparting strength and support to the device. The backing layer must provide protection from loss to the environment of the active agent and other components of the carrier composition, and prevent passage of substances into the transdermal system. Materials typically used as backing layers include plastic films, foils, papers and a variety of polymeric substances as described, for example, in U.S. Pat. Nos. 4,994,278 and 5,656,286.

In order to produce a transdermal drug delivery system intended to deliver an active agent locally, for example, for relief of pain or inflammation, flexibility and comfort become critical to the system's characteristics since many of the application sites are greatly contoured or subject to frequent movement. Conventional backing layers made of films are undesirable. If the backing layer is of sufficient thickness to provide the needed strength and support for the active agent carrier composition, then it typically lacks the elongation properties to provide the flexibility needed to maintain contact with the application site, as well as being uncomfortable. Conversely, if the backing layer is of sufficient thinness to provide the needed elongation properties that impart the flexibility needed to maintain contact with the application site, then it typically fails to provide the strength and support for the active agent carrier composition, as well as protection of loss from the environment.

Consequently, "soft" backings similar in appearance to the padded covering used in common stick-on bandages, such as cloth, woven and foamed materials, were utilized to achieve the needed elongation and support properties.

While variations exist in transdermal systems incorporating these soft backings, such systems intend these backing layers to serve not only as the outer protective surface, but also as the depot or storage location for receiving and retaining all or some of the active agent. In other words, the backing layer is or becomes infiltrated with the drug itself, or with a solution or mixture of the drug and a suitable solvent or polymer carrier. Typically, the active agent carrier is in a non-finite form such as a gel, ointment, liquid and the like.

Because the backing layer must therefore receive and absorb the active agent, (a) stability and potency of the drug and (b) porosity or occlusiveness of the backing layer which affects the degree of penetration of the drug and/or carrier composition into the backing layer, become important factors which often present problems with such devices.

For example, U.S. Pat. No. 5,741,510 describes a transdermal patch comprising a porous backing layer for receiving a pressure-sensitive drug containing hydrogel. The drug containing hydrogel is required to substantially penetrate into the backing layer. In order to prevent the hydrogel from becoming too viscous to properly penetrate the backing layer, the hydrogel requires chilling to keep it sufficiently fluid. The porosity of the backing layer consequently becomes important to achieve the necessary degree of penetration as well as to provide a non-occlusive patch (i.e., permit permeation of water vapor out of the system). Since the hydrogel also functions as the adhesive means for attachment of the device to the user, its application must be further controlled so as to also remain sufficiently on the surface of the backing layer.

U.S. Pat. No. 5,635,201 discloses a method and apparatus for manufacturing a wound dressing. The method includes coating an upper surface of a perforated backing material with a curable silicone mixture, blowing cold air onto the underside of the backing material, and applying heat to the silicone mixture until it is cured to a silicone gel. The cold air is applied by an air blowing unit to remove an applied silicone mixture from pores in the backing material, thereby maintaining the porosity of the wound dressing. The cold air further prevents the silicone mixture from curing before it has time to spread over the backing material.

In order to prevent the active agent and any solvents and/or polymer carrier for the active agent from passing outwardly and through the outer surface of the backing layer, some devices add a barrier layer to such outer surface. For example, U.S. Pat. No. 5,716,621 discloses the use of a moisture vapor permeable barrier layer bonded to the outer surface of a foam backing layer. The backing layer is used as the depot for the drug and its carrier composition. Since it is essential that the barrier layer be moisture vapor permeable, the patent further teaches nonadhesive techniques as the preferred method of bonding the barrier layer to the upper surface of the backing layer. Since such a transdermal system does not use a drug carrier composition which can also function to affix the system to the user, a separate adhesive means must be deposited on the inner surface of the backing layer. Such a system creates further complications.

For example, if the adhesive is incompatible with the backing layer, the attachment of the transdermal device to the user will be less than satisfactory, especially considering such devices are often desired to be worn continuously for an extended period of time and must be maintained properly in place throughout the entire period if the device is to effectively deliver a therapeutic amount. It is also important that the adhesive generally remain on the surface of the backing layer rather than fill or penetrate the cells or micropores of the backing layer, which can hinder or prevent the delivery system from delivering a therapeutically effect amount.

Stated differently, the adhesive must keep the transdermal device in intimate contact with the skin or mucosa by anchoring properly to both the backing layer and to the skin or mucosa, but without interfering with the backing layer's function of being the drug depot.

A number of techniques have been suggested for achieving such results. For example, in some devices the adhesive is applied to the backing layer in a pattern of coated and noncoated areas in order to leave some open areas of the backing layer for the drug to pass through. Alternatively, in transdermal devices made in particular shapes, the adhesive is often applied around the perimeter of the patch or in concentric circles, in yet another attempt to provide the necessary adherence to the skin, while permitting the concurrent necessary transfer of the active agent out of the backing layer. Such techniques often provide less than satisfactory results.

It is therefore an object of this invention to avoid the manufacturing and performance difficulties that are often encountered when the backing layer also functions as the substrate or storage location for the active agent and/or for the adhesive used to affix the system to the user, but still provide a flexible transdermal system which is able to conform to and remain in intimate contact with the site of topical application.

It is another object of this invention to provide a flexible transdermal system that comprises a backing layer lined with a barrier film of sufficient strength to support and anchor the other components of the transdermal system yet not interfere with the desired flexibility of the system.

It is also an object of this invention to provide a flexible transdermal system in which the barrier film lined backing layer does not "delaminate" (i.e., separate) during use of the system or upon its removal from the site of topical application.

It is a further object of this invention to provide a flexible transdermal system for delivery of active agents to a site of topical application in need of anti-inflammatory, analgesic or anesthetic therapy, such as knees, ankles and elbows, while still providing the flexibility required to remain in intimate contact with such topical application site and effect the needed therapy over the entire intended duration of use.

It is still a further object of this invention to provide a flexible transdermal system that can comfortably conform to and remain in substantially intimate contact during topical application with sites which are generally subject to frequent movement, flexing or bending, or are greatly contoured, such as knees, ankles and elbows, for at least 24 hours, and even up to 72 hours.

SUMMARY OF THE INVENTION

The foregoing and other objects and advantages are achieved by this invention which provides a transdermal drug delivery system that comprises a flexible, soft backing layer which is lined, on the side to face the application site, with a liquid impermeable barrier film, so as to prevent the active agent and/or solvent and/or carrier composition for the active agent, from penetrating into the backing layer.

The barrier film provides sufficient strength and support to anchor the other components of the transdermal system during the system's use, and yet does not interfere with the function of the backing layer—to allow the system to conform (i.e., flex and stretch) with movement at application site but remain substantially in intimate contact with the application site. Particularly preferred embodiments include backing layers comprising woven and non-woven fabrics, and foams.

In a particular embodiment, the barrier film layer is bonded to the backing layer by an adhesive to further reduce any interference with the system's ability to flex and stretch during topical application.

BRIEF DESCRIPTION OF THE DRAWING

A more complete appreciation and comprehension of the invention is facilitated by reference to the following detailed description when considered in conjunction with the accompanying drawing, in which.

Figure 1:
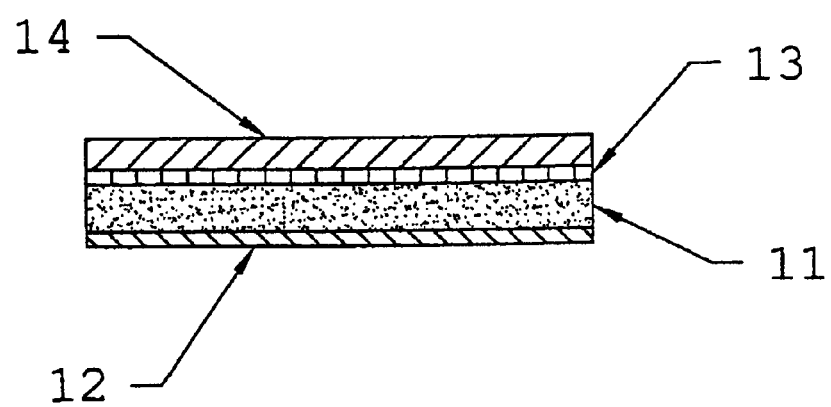
FIG. 1 is a cross-sectional schematic illustration of a transdermal drug delivery device according to the present invention.

It should be noted that the drawing is not necessarily to scale, but that the elements have been expanded to show more clearly the various aspects of a device according to the present invention.

DETAILED DESCRIPTION OF THE INVENTION

One embodiment of a transdermal drug delivery system in accordance with this invention is shown generally in FIG. 1. The transdermal drug delivery system 10 comprises a defined geometric shape having an active agent carrier composition layer 11 which has a release liner 12 on one side and the barrier film layer 13 on the other side. The barrier film layer 13 is joined to the backing layer 14 on the side opposite the active agent carrier composition layer 11. Removal of the release liner 12 exposes the active agent carrier composition layer 11, which layer functions as both the drug carrier and as the means of affixing the transdermal system 10 to the skin or mucosa of the user.

The principles of the invention will apply equally to reservoir-type drug delivery systems that comprise an adhesive layer or means to affix the system to the user which is separate from the active agent carrier composition layer 14. One or more optional layers, such as rate controlling membranes, may also be incorporated into the drug delivery system provided such additional layers do not significantly interfere with the transdermal system's ability to flex and stretch with movement during topical application, and with substantially maintaining intimate contact with the application site.

The term "topical" or "topically" is used herein in its conventional meaning as referring to direct contact with an anatomical site or surface area on a mammal including skin, teeth, nails and mucosa.

The term "mucosa" as used herein means any moist anatomical membrane or surface on a mammal such as oral, buccal, vaginal, rectal, nasal or ophthalmic surfaces.

The term "transdermal" as used herein means passage into and/or through skin or mucosa for localized or systemic delivery of an active agent.

As used herein, "therapeutically effective" means an amount of an active agent that is sufficient to achieve the desired local or systemic effect or result, such as to prevent, cure, diagnose, mitigate or treat a disease or condition, when applied topically over the duration of intended use.

The key element of this invention is the combination of a soft and flexible backing layer 14 with a barrier film layer 13 to achieve the desired wear and performance properties of strength, comfort, elongation, and flexibility with drug stability and delivery to be therapeutically effective, particularly with drugs intended for localized effect.

The barrier film layer 13 may be joined or affixed to the backing layer 14 by any conventional or known means of bonding. The bond created must however be of sufficient strength to inhibit or minimize delamination of the barrier film layer 13 from the backing layer 14 as the transdermal system is subjected to flexing and stretching encountered during topical application, or upon removal of the transdermal system from the application site. While nonadhesive techniques of joining the surfaces of the barrier film layer 13 to the backing layer 14, such as flame or heating bonding, or vacuum lamination, produce bonds of greater strength and rigidity than adhesive techniques, they may be disadvantageous by reducing the overall flexibility and conformability of the transdermal system during topical application. The transdermal system's ability to flex and stretch with movement during topical application yet substantially maintain intimate contact with the application site is a critical requirement. Accordingly, adhesives are the preferred means to join the barrier film layer 13 to the backing layer 14.

Suitable adhesives include any natural or synthetic material that is capable of adhering to a surface and remaining permanently tacky. Preferred adhesives are pressure-sensitive adhesives and include all of the non-toxic natural and synthetic polymers known or suitable for use in transdermal systems as hydrophobic adhesives, such as polyacrylates, polysiloxanes, silicones, rubbers, polyisobutylenes, polyvinylethers, polyurethanes, styrene/butadiene polymers, polyether block amide copolymers, ethylene/vinyl acetate copolymers, vinyl acetate based adhesives, and combinations and mixtures thereof.

An adhesive is a pressure-sensitive adhesive within the meaning of the term as used herein if it has the properties of a pressure-sensitive adhesive per se or if it functions as a pressure-sensitive adhesive by admixture with tackifiers, plasticizers or other additives.

Particularly preferred pressure-sensitive adhesives are low molecular weight adhesives. The term "low molecular weight" means that the adhesive is not substantially cross-linked, and has a molecular weight of less than about 1,000,000.

In general, a low molecular weight adhesive has a low viscosity and/or internal cohesiveness, thereby permitting the adhesive to remain fluid enough to migrate slightly into the backing layer when applied, rather than remain solely on the surface of the backing layer 14. This desired fluidity and slight penetration of the adhesive into backing layer helps to ensure a bond of sufficient strength to prevent or minimize delamination between the barrier film layer 13 and the backing layer 14. A low molecular weight adhesive tends to further remain more pliable and therefore allows for greater flexibility and comfort during topical application, which is essential to achieve optimal performance of the transdermal system.

While a high molecular weight adhesive could be heated or cooled, as the case may be, in order to prevent the adhesive from becoming too viscous to permit penetration into the backing layer 14, use of such an adhesive when cured or hardened may interfere with the transdermal system's desired ability to flex and stretch during topical application.

The adhesives particularly useful in practicing this invention are polyacrylates of one or more monomers of acrylic acids or other copolymerizable monomers. Polyacrylate adhesives also include polymers of alkyl acrylates and/or methacrylates and/or copolymerizable secondary monomers, or monomers with functional groups, and in particular hydroxy functional groups. The term "polyacrylate" is intended to be used interchangeably with the terms acrylic, acrylate and polyacrylic as used herein and as known in the art. Such polyacrylate adhesives preferably have a molecular weight of about 250,000 to about 750,000, and more preferably of about 300,000 to about 600,000.

Suitable low molecular weight acrylic adhesives are commercially available and include those sold under the trademarks DURO-TAK® 387-2510/87-2510 by National Starch and Chemical Company, Bridgewater, N.J., and GELVA® Multipolymer Solution 1151 by Solutia, Inc., St. Louis, Mo.

The appropriate amount of adhesive to be used for joining barrier film layer 13 to backing layer 14 is that amount which will provide a bond of sufficient strength between the barrier film layer 13 and the backing layer 14 to prevent delamination during topical application of the system, and more importantly, upon removal of the system from the application site. Such amount can be determined by routine testing.

In the practice of preferred embodiments of the invention, the low molecular weight acrylic adhesives can be applied to a thickness from about 2.0 mils to about 10.0 mils, and more preferably from about 4.0 mils to about 7.0 mils or, on a dry weight basis, from about 2.0 mg/cm$^2$ to about 7.5 mg/cm$^2$, and more preferably from about 2.5 mg/cm$^2$ to about 5.0 mg/cm$^2$.

Alternatively, the barrier film layer 13 and backing layer 14 may be prepared by coextrusion, thereby eliminating the need for use of a separate manufacturing step for bonding the two separate layers. Coextrusion also eliminates the processing parameters that must be carefully controlled when using adhesive and nonadhesive bonding techniques to produce a bond of sufficient strength to prevent or minimize delamination.

The barrier film layer 13 can be of any material well known in the art that is generally applicable to use as the backing layer in transdermal drug delivery systems, for example those described in U.S. Pat. No. 4,994,278 incorporated herein by reference. Preferably, the barrier film layer 13 is a thermoplastic material of polyester, polyethylene and ethylene copolymers, ethylene/vinyl acetate, polypropylene, polyurethane, ethylene/vinyl alcohol, polyvinyl alcohol, polyvinyllidene, polyolefin, Surlyn® (thermoplastic polymers ionically crosslinked containing both hydrogen and ionic bonds, and derived from ethylene/methacrylic acid copolymers, sold by Dupont, Wilmington, Del.), and mixtures, combinations and laminates thereof.

A critical requirement of the barrier film layer 13 of this invention is that it be substantially impermeable to passage of the drug and any solvents, polymers and other ingredients which can comprise the active agent carrier composition layer 11. The barrier film layer 13 must also be sufficiently compatible with the drug and with any solution or mixture of the drug and suitable polymer carrier so as not to degrade in their presence under normal conditions of use and storage. Nor should the barrier film layer 13 substantially degrade the drug or its carrier composition. Accordingly, selection of an appropriate material will, in each instance, be dependent on the particular drug intended for topical application.

Thermoplastic films suitable for use as the barrier film layer 13 generally are impermeable or occlusive to moisture or have negligible moisture vapor transmission rates (i.e., permeation of water vapor to and from the transdermal system). Non-occlusive thermoplastic materials (i.e., ones which will allow moisture vapor to significantly evaporate through it) can also be used but are not essential in practicing this invention.

In a preferred embodiment, the barrier film layer 13 is a polyester film possessing an average thickness equal to or less than about 1.0 mils, and more preferably from about 0.10 mils to about 0.75 mils, and most preferably from about 0.10 mils to about 0.3 mils. Particularly preferred polyester films are those commercially available and sold under the trademark Mylar® Type S films by Dupont, Wilmington, Del. In another preferred embodiment, the barrier film lining is a polyvinyl alcohol (which exhibits excellent elongation properties) in an average thickness of equal to or less than about 2.5 mils. Other thermoplastic films, as well as natural and synthetic rubbers, can also be used up to an average thickness of about 4.0 mils, provided such materials do not significantly interfere with the transdermal system's ability to flex and stretch with movement topical application yet substantially and comfortably maintain intimate contact with the application site.

The backing layer 14 can be of any material well known in the art for use as the backing in transdermal systems, provided that such materials in their as-manufactured or finished state are flexible and soft, and not cast or made into films excepting natural and synthetic rubbers. Suitable materials include non-woven fabric such as fibers of cellulose, polyester, cotton and the like which may be mixed with a unifying or sizing resin or emulsion, for example, an acrylic or latex; woven fabrics such as acetate polymer cloth, cotton or silk cloth or other cloth formed from a synthetic polymer, for example, nylon, polyester or polyacetate; and foams of thermoplastic/elastomeric materials. In the practice of preferred embodiments of the invention, the backing layer 14 can be a foam of polyolefin, polyurethane, polyvinyl chloride, polyethylenes, polypropylenes, polystyrenes, polyvinyl alcohols, ethylene/vinyl acetate copolymers, vinyl acetates, and combinations and mixtures thereof. Neither the porosity of the foam nor whether it is open-celled or closed-celled is essential in practicing the invention.

Since the transdermal system's ability to flex and stretch with movement at the application site, yet substantially and comfortably maintain contact, is an essential feature of the invention, any thickness of the backing layer 14 that is able to satisfy such criteria, taking the thickness of the other elements of the invention into account, can be used. In general, the thickness of the backing layer 14 can be up to 250 mils or more, depending on the elasticity or flexibility of the material. In preferred embodiments employing foams, in particular polyethylene and polyethylene/vinyl acetate copolymer foams such as VOLARA® or MINICEL® foams (both commercially available from Voltek, Inc., Lawrence, Mass.), a thickness from about 10 mils to about 100 mils, more preferably from about 10 mils to about 70 mils, and most preferably from about 10 mils to about 40 mils, will satisfy the criteria.

As used herein, the term "active agent" (and its equivalents, "agent," "drug," "medicament" and "pharmaceutical") is intended to have the broadest meaning and includes at least one of any therapeutic, prophylactic, pharmacological or physiological active substance, cosmetic and personal care preparations, and mixtures thereof, which is delivered to a mammal to produce a desired, usually beneficial, effect.

More specifically, any active agent which is capable of producing a pharmacological response, localized or systemic, irrespective of whether therapeutic, diagnostic, cosmetic or prophylactic in nature, is within the contemplation of the invention. It should be noted that the active agents or drugs can be used singularly or as a mixture of two or more agents or drugs, and in such amounts so as to achieve the desired effect or result, such as to prevent, cure, diagnose, mitigate or treat a disease or condition, as the case may be.

Specific drugs that are useful in practicing the invention include: topically delivered local anesthetics such as benzocaine, procaine, tetracaine, dibucaine, lidocaine, bupivicaine, dyclonin, etidocaine, mepivicaine, butamen picrate, dimethisoquin, cyclomethylcaine sulfate, and the like; analgesics and anti-inflammatory agents such as buprenorphin, butophanol tartrate, acetaminophen, fentanyl, mefenamic acid, flutenamic acid, diclofenac, oxyphenbutazone, phenybutazone, ibuprofen, fenoprofen, flurbiprofen, naproxen, menthol, methyl salicylate, peroxicam, phenol, salicylic acid, benzyl alcohol, camphor, camphorated metacresol, juniper tar, resorcinol, allyl isothiocyanate, capsaicin, and the like; corticosteroids such as alclometasone dipropionate, amcinocide, hydrocortisone, betamethasone, desoximetasone, clobetasol, fludrocortisone, flurandrenolide, halcinonide, halobetasol, estradiol, testosterone, progesterone, fluticasone, clobetasol, dexamethasone, dexonide, fluocinolone, flucinonide, mometasone furoate, triamcinolone, and the like; antibiotics such as bacitracin, chlortetracycline, chlorhexadine, clindamycin, cliquinol, neomycin, polymyxin B sulfate, erythromycin, gentamicin, sulfathiazole, sulfacetamide, sulfabenzamide, oxytetracycline, tetracycline, and the like; antimicrobial agents such as benzaikonium, hexaclorophene, mafenide, nitrofurazone, nystatin, acetosulfamine, clortrimazole, povidone-iodine, and the like: antifungal agents such as amphotericin B, butoconazole, cetylpyridinium, chlorxylenol, cyclopirox olamine, clioquinol, clotrimazole, sulconazole, nystatin, oxyconazole, econazole, ketoconazole, miconazole, naftifine, pentamycin, pyrrolinitrin, terbinafine, triacetin, and the like; debriding agents such as deoxyribonuclease, collagenolytic, debridement, fibrinolytic or proteolytic enzymes, papain, papain-urea, and the like; antihistamines such as chlorcyclizine, diphenylhydramine, tripelennamine, and the like; antiepileptics such as nitrazepam, meprobamate, clonazepam, and the like; coronary vasodilators such as nitroglycerin, dipyridamole, erythritol, tetranitrate, pentaerythritol tetranitrate, propatylnitrate, and the like; dermatologicals such as retinal, retinol, retinoic acid and their derivatives, hydroxyacids, alphaketoacids, and the like; estrogens such as conjugated estrogens, esterified estrogens, estropipate, 17-β estradiol, 17-β estradiol valerate, equilin, mestranol, estriol, estrone, and ethinyl estradiol; progestational agents such as progesterone, 19-norprogesterone, norethindrone, norethindrone acetate, melengestrol, chlormadinone, ethisterone, medroxyprogesterone, hydroxyprogesterone, ethynodiol, norethynodrel, 17-alpha-hydroxyprogesterone, dydrogesterone, dimethisterone, ethinylestrenol, norgestrel, demegestone, promogestone, ethinylestrenol, norgestrel, demgestone, promegestone, and megestrol; other durgs such as benzoyl peroxide, podofilox, prednisolone, prednisone, masoprocol, nicotine, scopolamine, methylphenidate, testosterone, methyltestosterone, triptans such as sumatriptan, fluorouracil, hydroquinone, monobenzone, tretinoin and acyclovir.

A transdermal drug delivery system in accordance with this invention is particularly useful in substantially localized topical administration of active agents in mammals for relief of pain or inflammation associated, for example, with backaches, arthritis, muscular aches and strains, at the site of application, and include analgesics such as salicylates menthol and camphor, non-steroidal anti-inflammatory agents such as ketoprofen and ibuprofen, anesthetics such as lidocaine and benzocaine, corticosteroids such as hydrocortisone, anti-inflammatory agents such as capsaicin, and keatolyic agents such as salacylic acid.

Since many of the application sites for relief of pain involve joints such as elbows, knees, ankles and other areas of the body that are greatly contoured or subject to frequent movement, the present invention provides excellent support and strength to retain the active agent carrier composition layer 11 yet allows the system to stretch, fold and crease during topical application without significant loss of contact with the skin or mucosa.

The active agent carrier composition 11 can be prepared in any manner known to those of skill in the art. Preferred methods of preparation include those described in U.S. Pat. Nos. 5,474,783; 5,656,286; 5,234,957; 5,332,576 and 5,446,070, and U.S. Ser. No. 09/161,312, all of which are incorporated herein by reference. After the active agent carrier composition 11 is prepared, it is coated or applied to the release liner 12 at a controlled specified thickness. The carrier composition/release liner composite is then passed through an oven in order to evaporate any solvents with which the adhesive or carrier composition may have been formulated.

Similarly, any adhesive used to join the barrier film layer 13 to the backing layer 14 is coated or applied to the backing layer 14, passed through an oven to also evaporate any solvents with which the adhesive may have been formulated, and then laminated to the barrier film layer 13.

The finished transdermal drug delivery device 10 is manufactured by laminating the carrier composition side of the carrier composition/release liner composite to the barrier film of the barrier film lined backing layer composite, and then cutting into appropriate sizes, shapes and patterns.

The order of steps, amount and types of components, the methods of coating and the manufacturing process, for example continuous or semi-continuous, may be adjusted and/or changed by those skilled in the art and will also give desirable results.

The configuration of transdermal drug delivery system 10 can be in any shape, preferably a defined geometric shape, and size (i.e., surface area of application) as is necessary or desirable. The shape is achieved by conventional techniques, for example, cutting or punching, and such techniques are described, for example, in U.S. Pat. Nos. 5,032,207; 5,405,486 and 5,656,285. The intended site of topical application is an important factor in determining the size and shape of an individual unit or delivery system of the present invention, and can be adjusted by those skilled in the art as is necessary to effect therapy. Typically the size should not exceed 100 cm$^2$. Preferred sizes range from about 1.5 cm$^2$ to about 60 cm$^2$, and more preferred range from about 10 cm$^2$ to about 50 cm$^2$, and optimally from about 20 cm$^2$ to about 40 cm$^2$.

The following example further illustrates the transdermal drug delivery system 10 of the invention, but should not be considered as limiting in any way the invention being disclosed herein.

EXAMPLE 1

A low molecular weight acrylic pressure-sensitive adhesive such as DURO-TAK® 387-0510 is coated at an average thickness of about 7.0 mils onto a polyethylene/ethylene vinyl acetate, cellular foam backing layer such copolymer as VOLARA® having an average thickness of about 30.0 mils and passed through an oven to evaporate any solvents. A polyester barrier film such as MYLAR® Type S having an average thickness of about 0.2 mils is then laminated to the adhesive side of the adhesive/backing layer composite, and wound into a roll.

Appropriate amounts of starting materials comprising the active agent carrier composition are blended together with a processing solvent (such as isopropyl alcohol) to form a homogeneous mixture, which is then coated onto a suitable release liner such as Scotch Pak® 1020 (manufactured by 3M Corporation, St. Paul, Minn.). The coated release liner is passed through an oven to evaporate any solvents, and yields the following ingredient concentrations on a weight percent (%) by dry weight of the total active agent carrier composition layer 11.

| Ingredient | w/w % |
| --- | --- |
| Acrylic Adhesive (DURO-TAK ® 87-4852) | 51.0 |
| Silicone Adhesive (BIO-PSA 7-4502) | 12.0 |
| Polyvinylpyrrolidone (Kollidon ® 30) | 6.0 |
| Oleic Acid | 14.0 |
| Ketoprofen | 17.0 |
| | 100.0 |

As the coated release liner exits the oven, it is laminated to the barrier film of the barrier film lined backing layer composite, and then die-cut into individual transdermal systems.

Finished units of transdermal systems incorporating the formulation of Example 1 were prepared with four different backings and analyzed for drug stability. Six samples with each different backing were prepared—three samples were heat sealed in a foil/paper laminate pouch (to prevent any environmental drug loss), and placed in an oven at 80° C. to approximate six moth shelf life stability, and the other three samples were placed at standard room temperature and assayed at initial time zero ($T_0$). The pouched transdermal systems were assayed four days later and results were compared to the initial ($T_0$) assayed units for drug potency changes. The results are set forth in Table I.

TABLE I

| Backing Material | Initial Potency (mg/g) | 4 Day Potency (mg/g) | % Potency loss |
| --- | --- | --- | --- |
| Dow Backing 2014 (2 mil) | 168.40 | 159.63 | 5.21 |
| Volara ® Foam (10 mil) | 173.82 | 134.08 | 22.87 |
| Non-Woven (15 mil) | 175.86 | 173.56 | 1.31 |
| Non-Woven (20 mil) | 176.72 | 176.40 | 0.18 |

The non-woven backing is a laminate of rayon/polyester and is non-occlusive to drug. While drug loss results were favorable, subsequent testing found they were unsuitable because of their inability to provide sufficient drug permeation rates. Dow 2014 is a coextruded backing five layer film of polyethylene/ethylene vinyl acetate/polyvinylidene chloride/ethylene vinyl acetate/polyethylene which is soft and occlusive but did not provide the desired elongation properties.

Since the tested backings failed to provide all the desired properties, a film of polyethylene and of polyester was tried as a barrier layer in conjunction with the foam to protect the carrier composition from the detrimental foam effects but maintain the desired elongation properties of the foam. Stability tests were run as described above with the following results set forth in Table II.

TABLE II

| Backing Material | Initial Potency (mg/g) | 4 Day Potency (mg/g) | % Potency loss |
| --- | --- | --- | --- |
| Volara Foam (10 mil)/Polyethylene (1.0 mil) | 189.93 | 130.82 | 42.24 |
| Volara Foam | 229.60 | 181.81 | 20.81 |
| Dow Backing 2014 (2.0 mil) | 166.32 | 155.63 | 6.43 |
| Volara Foam (10 mil)/Polyester (0.20 mil) | 171.33 | 164.33 | 4.09 |
| Volara Foam (10 mil)/Polyester (0.25 mil) | 172.38 | 161.80 | 6.14 |

The data indicates that polyethylene was completely unsuitable as a barrier to ketoprofen loss. Unprotected foam exhibited much worse stability than Dow Backing 2014, but both backings were improved upon by utilizing a thin polyester barrier film on the Volara foam which demonstrated the best product stability.

What is claimed is:

1. A flexible transdermal drug delivery system that substantially maintains contact with movement at the topical site of application, comprising
   (a) a carrier composition layer comprising a therapeutically effective amount of one or more drugs;
   (b) a flexible, soft backing layer consisting essentially of a cellular foam which is substantially permeable to the carrier composition;
   (c) a barrier layer substantially compatible with and impermeable to the drug and carrier composition and consisting essentially of a film of thermoplastic polymers and rubbers having an average thickness of about 0.1 mils to about 4.0 mils and an inner and outer surface, the outer surface of which is joined to the backing layer by means of a low molecular weight adhesive or by co-extrusion, and the inner surface of which is in contact with the carrier composition.

2. The drug delivery system of claim 1, wherein the barrier layer is a thermoplastic polymer selected from the group consisting of polyester, polyolefins, polyvinyl alcohols, acrylonitrile-methyl acrylate copolymers, and multipolymers thereof.

3. The drug delivery system of claim 2, wherein the thermoplastic polymer is a polyester having an average thickness of about 0.1 mils to about 1.0 mils.

4. The drug delivery system of claim 2, wherein the thermoplastic polymer is polyvinyl alcohol having an average thickness of about 0.1 mils to about 2.5 mils.

5. The drug delivery system of claim 1, wherein the backing layer is selected from the group consisting of polyolefins, polyurethanes, polyvinyl chlorides polystyrenes, ethylene/vinyl acetate copolymers, vinyl acetates, polyethylene/vinyl acetate copolymers.

6. The drug delivery system of claim 1, wherein said barrier layer is substantially impermeable to water vapor.

7. The drug delivery system of claim 1, wherein the one or more drugs is selected from the group consisting of analgesics, non-steroidal anti-inflammatory agents, anesthetics, corticosteroids and anti-inflammatory agents.

8. The drug delivery system of claim 7, wherein the one or more drugs includes a non-steroidal anti-inflammatory agent selected from the group consisting of ibuprofen, ketoprofen, fenoprofen, flurbiprofen, naproxen and peroxicam, and combinations thereof.

9. The drug delivery system of claim 7, wherein the one or more drugs includes an anesthetic selected from the group consisting of benzocaine, procaine, tetracaine, dibucaine, lidocaine, bupivicaine, dyclonin, etidocaine, mepivacaine, and combinations thereof.

10. A flexible transdermal drug delivery system that substantially maintains contact with movement at the topical site of application comprising: (a) a carrier composition layer comprising a therapeutically effective amount of one or more drugs; (b) a flexible, soft backing layer consisting essentially of a cellular foam selected from the group consisting of polyethylene, vinyl acetates, ethylene/vinyl acetate copolymers, wherein the carrier composition is excluded from the backing layer; (c) a barrier layer substantially compatible with and impermeable to the one or more drugs and carrier composition consisting essentially of a film of a thermoplastic polymer selected from the group consisting of polyester, ethylene vinyl alcohol and acrylonitrile-methyl acrylate copolymers having thickness of up to 2.5 mils and an inner and outer surface of which of joined to the backing layer by means of a low molecular weight adhesive, and the inner surface of which is in contact with carrier composition.

11. The drug delivery system of claim 10, wherein the backing layer is a polyethylene/vinyl acetate copolymer having a thickness in the range of about 10 mils to about 100 mils and the barrier layer is polyester.

12. A method for topical administration of a therapeutically effective amount of one or more drugs to a mammal in need of relief from pain or inflammation comprising the steps of topically applying a flexible transdermal delivery system for administration of one or more drugs to an area of the mammal which is contoured or generally subject to frequent movement, bending or flexing, and maintaining said system in substantially intimate contact with the area of topical application for the internet duration of use, wherein said flexible transdermal delivery system comprises: (a) a carrier composition layer comprising a therapeutically effective amount of one or more drugs selected from the group consisting of analgesics, non-steroidal anti-inflammatory agents, anesthetics, corticosteroids and anti-inflammatory agents; (b) a flexible, soft backing layer consisting essentially of a cellular foam, wherein the carrier composition is excluded from the backing layer; (c) a barrier layer substantially compatible with and impermeable to said one or more drugs and carrier composition consisting essentially of a film of a thermoplastic polymer selected from the group consisting of polyester, ethylene vinyl alcohol and acrylonitrile-methyl acrylate copolymers having an average thickness of up to 2.5 mils and an inner and outer surface, the outer surface of which is joined to the backing layer by means of a low molecular weight adhesive or by co-extrusion and the inner surface of which is in contact with the carrier composition.

13. The method according to claim 12 wherein the backing layer is selected from the group consisting of polyolefins, polyurethanes, polyvinyl chlorides, polystytrenes, ethylene/vinyl acetate, vinyl acetates, polyethylene vinyl acetate copolymers.

14. The method according to claim 12, wherein the backing layer is a polyethylene/vinyl acetate copolymer having a thickness in the range of about 10 mils to about 100 mils and the barrier layer is polyester.

15. A method according to claim 12, wherein the drug is ketoprofen.

16. A method according to claim 12, wherein the topical administration of the one or more drugs is for substantially localized delivery.

\* \* \* \* \*